United States Patent [19]
Kvalo et al.

[11] Patent Number: 5,163,947
[45] Date of Patent: Nov. 17, 1992

[54] BIOPSY NEEDLE SPACER

[75] Inventors: Michael L. Kvalo, Oxford; Larry A. Roberts, Marietta, both of Ga.

[73] Assignee: C. R. Bard, Inc., Murray Hill, N.J.

[21] Appl. No.: 753,220

[22] Filed: Aug. 30, 1991

[51] Int. Cl.⁵ .............................................. A61B 10/00
[52] U.S. Cl. .................................... 606/151; 128/749; 24/457
[58] Field of Search ............................. 128/749–755; 606/151, 157, 167, 170–172, 185

[56] References Cited

U.S. PATENT DOCUMENTS

| | | | |
|---|---|---|---|
| 4,699,154 | 10/1987 | Lindgren | 128/754 |
| 4,917,100 | 4/1990 | Nottke | 128/754 |
| 5,092,870 | 3/1992 | Mittermeier | 128/749 |

OTHER PUBLICATIONS

Parker et al., Image-directed Percutaneous Biopsies with a Biopsy Gun, Radiology, vol. 171, No. 3, pp. 663–669 (Jun., 1989).

*Primary Examiner*—Max Hindenburg
*Attorney, Agent, or Firm*—Jones, Askew & Lunsford

[57] ABSTRACT

A needle spacer is disclosed for use with a biopsy needle assembly of the type which is coupled to a driving unit to effect movement of the needle assembly. The needle spacer maintains the biopsy needle assembly in a predetermined operational relationship until after the needle assembly is coupled to the driving unit. In the preferred embodiment, the needle spacer prevents the lid of the driving unit from being closed while the needle spacer is still in place on the needle assembly, thereby eliminating the possibility that the physician will forget to remove the spacer prior to firing the instrument. In a first alternate embodiment, the needle spacer is configured to interfere with movement of the needles within the driving unit while the spacer is still in place so that if the physician attempts to fire the instrument with the needle spacer still in place, the needles will not advance. In a second alternate embodiment, the needle spacer includes a readily visible flag which, even with the lid of the driving unit closed, will alert the physician that the needle spacer is still in place, thus reducing the possibility that the physician will forget to remove the spacer.

17 Claims, 3 Drawing Sheets

BIOPSY NEEDLE SPACER

TECHNICAL FIELD

The present invention relates generally to medical instruments for retrieving tissue specimens for biopsy purposes, and relates more specifically to an apparatus for positively maintaining the relative positions of a stylet and cannula of a coaxial biopsy needle assembly of the type used in an automatic dual stage biopsy instrument.

BACKGROUND OF THE INVENTION

In recent years, automated, spring-propelled dual stage automated tissue sampling devices have greatly simplified retrieval of tissue specimens for biopsy purposes. An example of such an instrument is disclosed in U.S. Pat. No. 4,699,154 to Lindgren et al. That patent discloses a driving unit having a pair of sequentially driven, spring-propelled slides for driving a coaxial needle assembly. The coaxial needle assembly comprises a cannula having a sharpened forward end and a stylet telescopically received within the cannula. The stylet and cannula each have needle heads mounted to their rearward ends which are removably coupled to the spring-propelled slides of the driving assembly. When the driving unit is actuated, the first slide is released to propel the stylet forward into the target tissue. As the tip of the stylet enters the target tissue, a section of the tissue enters a notch near the forward end of the stylet. At the instant the stylet reaches the forward end of its travel, the second slide is released, propelling the cannula forward over the stylet, shearing off the tissue specimen and capturing it within the forward end of the cannula. The needle is then withdrawn from the patient, and the needle assembly is removed from the driving unit to permit the tissue specimen to be recovered for biopsy.

Despite its significant advantages over prior art biopsy needles, the biopsy instrument disclosed in the aforementioned U.S. Pat. No. 4,699,154 suffers certain disadvantages when used in conjunction with CT scan. After the physician has directed the needle assembly to the desired tissue location identified by the CT scan, and before actuating the driving unit to retrieve a tissue specimen, the patient must be rescanned to verify the location of the needle tip with respect to the lesion. This rescanning cannot be done with the needle coupled to the driving unit, because the weight of the drive mechanism would not be supported by the needle sticking in the patient, and because the needle drive mechanism would not fit within the gantry of the CT scanner. Thus, it is necessary to uncouple the needle assembly from the driving unit to rescan the patient.

A problem arises when the coaxial needle assembly is not coupled to its driving unit. Since the needle assembly is not intended for use separate from the driving unit, there is no mechanism by which the needles can be locked relative to one another. Since the stylet telescopes freely within the cannula, it is very easy for the needles to move relative to one another. Consequently, with the needle assembly uncoupled from the driving unit to permit CT scan, normal movements by the patient, e.g. aspiration, can cause relative displacement between the stylet and cannula. Since the slides of the driving unit are a predetermined distance apart, the needle head must be a corresponding distance apart for the needle assembly to be recoupled to the driving unit after CT scan. This requirement may necessitate the stylet and cannula to be moved relative to one another to conform the spacing between the needle heads to the spacing between the slides of the driving unit. Such movement may cause displacement of the tip of the needle with respect to the target tissue, thereby negating the confirmation obtained by the CT scan and possibly leading to an inaccurate tissue sample.

Consequently, there arose a need for a mechanism whereby the cannula and stylet of a needle assembly can be retained in predetermined, spaced apart relation while the needle assembly is uncoupled from its associated driving unit to permit CT scan.

An article by Parker et al., which appeared in RADIOLOGY, Vol. 17, entitled Image-directed Percutaneous Biopsies with a Biopsy Gun, discloses the use of a spacer member comprising a short length of longitudinally slit tubing designed to fit over that portion of the stylet between the cannula needle head and the stylet needle head. The spacer member maintains the stylet and cannula in the desired relationship when the needle assembly is not mounted to the driving unit. With the spacer member installed and the needle assembly uncoupled from the driving unit, the physician is able to manually direct the needle assembly to the site of the lesion with the spacer maintaining the stylet and cannula fixed relative to one another. With the needle in situ, the patient is rescanned to verify the location of the tip of the needle assembly with respect to the lesion. If necessary, the needle is repositioned, and the patient is rescanned. When the needle is properly positioned and the needle location has been verified, the spacer is removed from the needle assembly, and the cocked drive unit is mounted to the needle assembly. The biopsy instrument is then fired in the conventional manner to retrieve a tissue sample.

This approach suffers certain disadvantages in that, since the needle spacer is removed prior to the needle assembly being coupled to the driving unit, it is possible to experience some relative movement of the stylet and cannula, and hence possibly movement of the needle tip with respect to the target tissue, while attempting to couple the needle assembly to the driving unit. Further, if the needle assembly is coupled to the driving unit before the spacer is removed, it is easy for the physician to forget to remove the spacer before attempting to fire the instrument. Since the spacer maintains the respective needle heads at a fixed separation, the requisite relative telescoping movement of the coaxial needle assembly cannot be achieved with the spacer still mounted. Thus, when the physician actuates the trigger of the driving unit to fire the needles, the spacer may prevent either of the needles from advancing. Alternatively, triggering the driving unit with the spacer still mounted could result in both needles being fired simultaneously, rather than sequentially. In such an event, the tip of the stylet would never telescope forward of the cannula to expose the tissue receiving recess adjacent the forward end of the stylet, and no tissue specimen would be retrieved. To compound the problem, the instrument may appear to the physician to have been fired normally, so the physician will assume a tissue specimen has been retrieved and will withdraw the needle from the patient before realizing that a tissue specimen has not been captured. As a result, the physician would have to repeat the entire procedure, including repositioning the needle and rescanning to verify the position of the needle tip. Such a mistake would increase discomfort to the patient and increase the cost of the procedure, since physician time required to perform the procedure is increased.

SUMMARY OF THE INVENTION

As will be seen, the present invention overcomes these and other problems associated with the use of automated, spring-propelled, dual stage, automated tissue sampling devices in conjunction with computer tomography. Stated generally, the present invention comprises a needle spacer which maintains the biopsy needle assembly in predetermined relation until after the needle assembly is coupled to the driving unit. In the preferred embodiment, the needle spacer prevents the lid of the driving unit from being closed while the needle spacer is still in place on the needle assembly, thereby eliminating the possibility that the physician will forget to remove the spacer prior to firing the instrument. In a first alternate embodiment, the needle spacer is configured to interfere with movement of the needles within the driving unit while the spacer is still in place so that if the physician attempts to fire the instrument with the needle spacer still in place, the needles will not advance. In a second alternate embodiment, the needle spacer includes a readily visible flag which, even with the lid of the driving unit closed, will alert the physician that the needle spacer is still in place, thus reducing the possibility that the physician will forget to remove the spacer.

Stated somewhat more specifically, the present invention comprises needle spacer apparatus for use with a needle assembly and a driving unit. The needle assembly comprises a hollow first needle having a first needle head at the rearward end thereof and a second needle telescopically received within the hollow first needle and having a sharpened tip at the forward end thereof and a second needle head at the rearward end thereof. The first and second needle heads are relatively movable to an operational relationship wherein the sharpened tip of the second needle projects slightly beyond the forward end of the hollow first needle. The needle assembly is capable of being selectively coupled to the driving unit for effecting relative movement of the needles, and the driving unit includes a housing having a lid which can be selectively opened to permit the needle assembly to be coupled to the driving unit.

The needle spacer apparatus comprises means selectively mountable to the needle assembly for maintaining the needle heads in their operational relationship, and the means is configured to permit the needle assembly to be coupled to the driving unit with the means mounted thereto. In the preferred embodiment, the needle spacer apparatus is configured to prevent the lid of the driving unit housing from being closed while the needle spacer apparatus is mounted to the needle assembly, so that a user will not attempt to actuate the driving unit with the needle spacer apparatus mounted to the needle assembly. In a first alternate embodiment, the needle spacer apparatus is configured to prevent the driving unit from effecting movement of the needles while the needle spacer apparatus is mounted to the needle assembly, so that if a user attempts to actuate the driving unit with the needle spacer apparatus mounted to the needle assembly, the driving unit will not operate. In a second alternate embodiment, the needle spacer apparatus is configured to be visible from outside the housing while the needle spacer apparatus is mounted to the needle assembly, even when the lid of the housing is closed. Thus, a user will see that the needle spacer apparatus is still mounted to the needle assembly even with the lid closed and not attempt to actuate the driving unit with the needle spacer apparatus mounted to the needle assembly. In the disclosed example of the second alternate embodiment, the needle spacer apparatus comprises a length of ribbon attached to the needle spacer apparatus which will hang outside the housing and thereby be visible to the user, even when the lid of the housing is closed.

Thus, it is an object of the present invention to provide an improved biopsy needle spacer.

Another object of the present invention is to provide a biopsy needle spacer which will prevent operation of a biopsy tissue sampling device with the spacer still attached to the needle assembly.

It is another object of the present invention to provide a biopsy needle spacer which will discourage a user from attempting to actuate the driving unit with the biopsy needle spacer still attached to the needle assembly.

Still another object of the present invention is to provide a biopsy needle spacer which will prevent operation of the driving unit while the biopsy needle spacer is still attached to the needle assembly.

Other objects, features, and advantages of the present invention will become apparent upon reading the following specification, when taken in conjunction with the drawings and the appended claims.

DETAILED DESCRIPTION OF THE DISCLOSED EMBODIMENT

Figure 1:
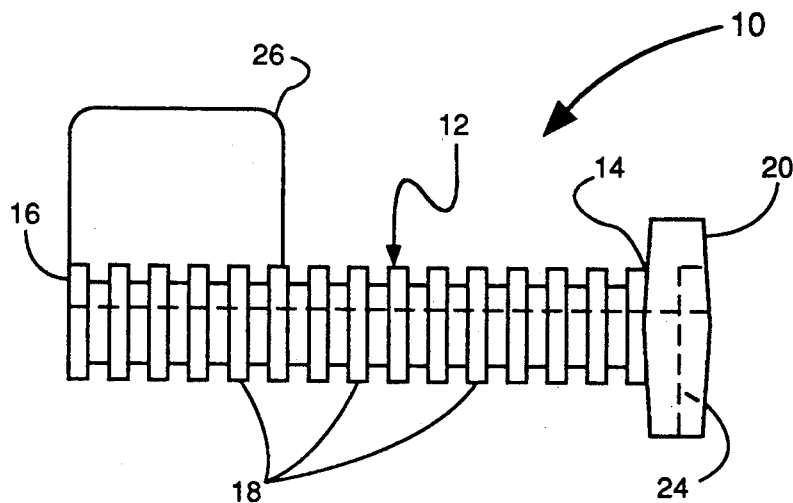
FIG. 1 is a side view of a biopsy needle spacer according to the present invention.
Figure 2:
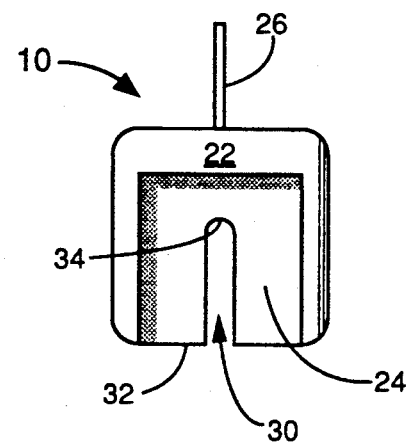
FIG. 2 is a front view of the biopsy needle spacer of FIG. 1.
Figure 3:
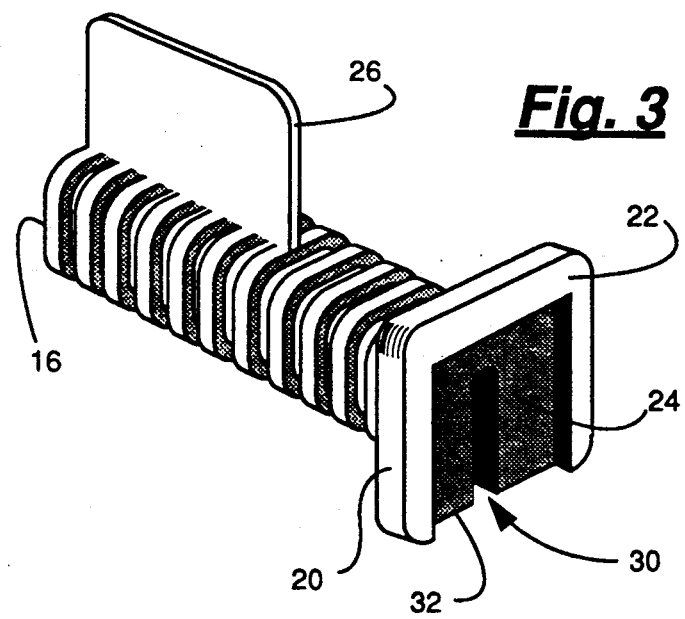
FIG. 3 is a perspective view of the biopsy needle spacer of FIG. 1.

Referring now to the drawings, in which like numerals indicate like elements throughout the several views, FIGS. 1-3 illustrate a preferred embodiment of a needle spacer 10 according to the present invention. The needle spacer 10 of the disclosed embodiment is molded from Krayton ™, a thermoplastic material available from Shell Chemical Company. For reasons which will be explained hereinbelow, it has been found that best results can be achieved when the needle spacer 10 is comprised of a relatively soft material, preferably 50–100 on the Shore A hardness scale. However, it will be understood that the material comprising the needle spacer is not critical, and that a more rigid material, e.g. hard nylon or plastic, may be used if desired.

The needle spacer 10 includes an elongated body 12 having a forward end 14 and a rearward end 16. The body 12 further comprises a plurality of decorative circumferential ribs 18. The needle spacer 10 has a transverse flange 20 formed at the forward end 14 of the body 12. The flange 20 includes a face 22 having a rectangular recess 24 formed in the lower portion thereof. The needle spacer 10 further has an upwardly projecting fin 26 formed on the upper surface of the body 12. The function and purpose of the recess 24 and the fin 26 will be more fully explained hereinbelow.

Referring now to FIG. 2, the biopsy needle spacer 10 has an upwardly extending slot 30 formed in the lower face 32 of the body 12. The slot 30 has a width dimensioned to receive the shaft of a biopsy stylet therewithin. The upper end 34 of the slot 30 terminates a point slightly above the central longitudinal axis of the body 12 such that a biopsy stylet positioned in the upper end 34 of the slot 30 will be approximately coaxially disposed with the needle spacer 10.

Figure 4:
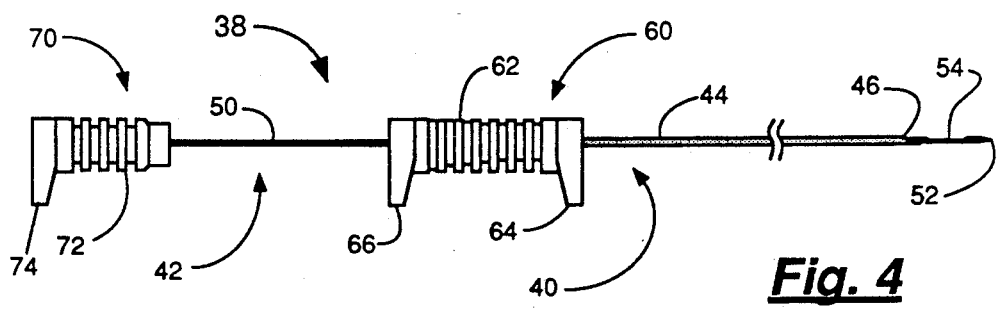
FIG. 4 is a side view of a prior art biopsy needle assembly of the general type with which the biopsy needle spacer of FIG. 1 is intended to function.

FIG. 4 depicts a prior art biopsy needle assembly 38 of the general type with which the needle spacer is intended for use. The biopsy needle assembly 38 is of a type commercially available from the Urological Division of C. R. Bard, Inc., of Covington, Ga., USA, and is sold under the trademark "Biopty-Cut." The biopsy needle assembly 38 includes a cannula 40 and a stylet 42. The cannula 40 comprises a hollow shaft 44 having a sharpened forward end 46. The biopsy stylet 42 comprises a shaft 50 which is telescopically received within the hollow shaft 44 of the cannula 40. The stylet shaft 50 has a sharpened tip 52 at its forward end and a tissue sample receiving recess 54 located adjacent the stylet's forward end.

At the rear end of the cannula 40 is a cannula needle head 60. The cannula needle head 60 comprises a body 62 having a plurality of decorative circumferential ribs formed thereon. Front and rear transverse flanges 64, 66 are formed at the front and rear ends of the body. The flanges 64, 66 are essentially rectangular in configuration and form the means whereby the cannula is coupled to a driving unit, as will be explained below. A stylet needle head 70 is provided at the rear end of the stylet 42 and includes a body portion 72 having a plurality of decorative circumferential ribs. The stylet needle head 70 has only a single transverse flange 74 formed at the rearward end of the body 72 which provides a means whereby the stylet is coupled to a driving unit.

Figure 5:
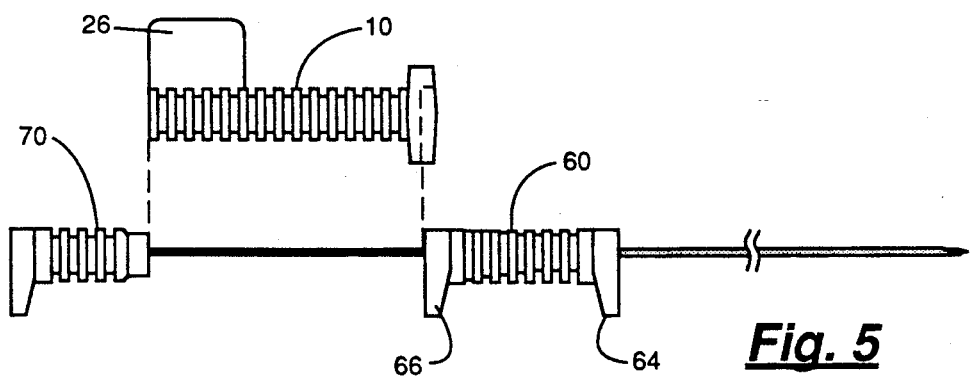
FIG. 5 is a side view illustrating the mounting of the biopsy needle spacer of FIG. 1 onto the biopsy needle of FIG. 4.

The interrelation between the biopsy needle spacer 10 and the biopsy needle assembly 38 is illustrated in FIGS. 5–8. Referring first to FIG. 5, the cannula 40 is telescoped forward over the stylet 42 such that the tissue sample receiving recess 54 adjacent the forward end of the stylet is concealed within the forward end of the cannula shaft 42, and only the sharpened stylet tip 52 protrudes beyond the forward end 46 of the cannula. In this position, the cannula needle head 60 and the stylet needle head 70 are spaced apart by a predetermined distance.

Figure 6:
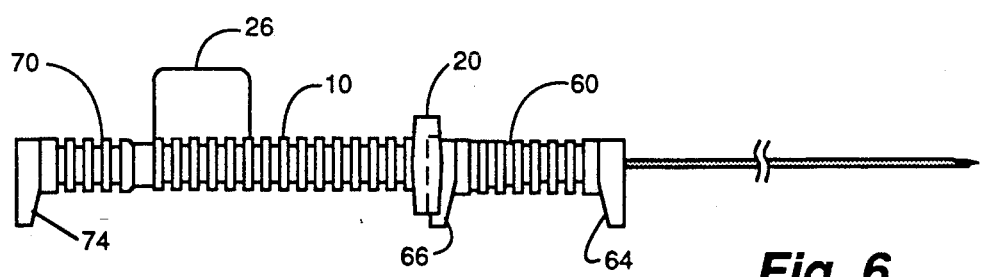
FIG. 6 is a side view of the biopsy needle spacer of FIG. 1 mounted onto the biopsy needle of FIG. 4.

Referring now to FIGS. 5 and 6, with the biopsy needle heads 60, 70 in their predetermined spaced apart relation, the biopsy needle spacer 10 slides down onto the biopsy needle assembly 38 between the needle heads. The exposed length of the stylet shaft 50 rearward of the cannula needle head 40 is inserted into the slot 30 in the bottom face 32 of the biopsy needle spacer 10 and received into the upper end 34 of the slot 30. The recess 24 in the front face 22 of the flange 20 of the needle spacer 10 is dimensioned to receive the rear transverse flange 66 of the cannula needle head 40 snugly therewithin. The rear end 16 of the biopsy needle spacer 10 bears against the forward end of the stylet needle head 42.

Figure 7:
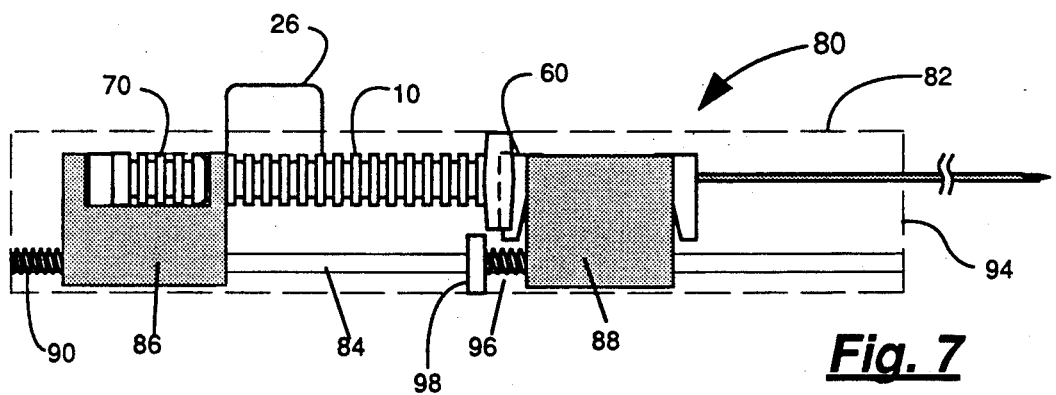
FIG. 7 is a side view of the assembly of FIG. 6 mounted to a biopsy needle driving unit, with the housing of the driving unit shown in phantom lines.

Referring now to FIG. 7, the biopsy needle assembly 38 with needle spacer 10 mounted thereto is coupled to a spring-propelled driving unit 80. The driving unit 80 is of the type described in U.S. Pat. No. 4,699,154 to Lindgren et al., which patent is incorporated herein by reference. This type of driving unit 80 is commercially available from the Urological Division of C. R. Bard, Inc., Covington, Ga., U.S.A., under the designation "Biopty". The driving unit 80 comprises a housing 82 having longitudinal rails 84 mounted therewithin. First and second carriages 86, 88 are slidably mounted on the rails 84 for longitudinal movement within the housing 82. A rear spring 90 is disposed between the rear wall 92 of the housing 82 and the first carriage 86 and biases the first carriage toward the forward end 94 of the housing. A second spring 96 is disposed between an intermediate wall 98 and the second carriage 88 and biases the second carriage toward the forward end 94 of the housing 82.

The needles 40, 42 of the biopsy needle assembly 38 are coupled to the slides 86, 88 of the driving unit 80, the stylet needle head 70 being coupled to the first slide 86 and the cannula needle head 60 being coupled to the second slide 88. When the biopsy needle assembly 38 is coupled to the driving unit 80, the spaced apart relation between the biopsy needle heads 60, 70 is controlled by the spacing between the first and second carriages 86, 88. The biopsy needle spacer 10 is configured such that it maintains the needle heads 86, 88 in the required spaced apart relation such that the needle assembly 38 can be mounted to the driving unit 80 without having to perform any relative movement between the stylet 42 and the cannula 40.

Figure 8:
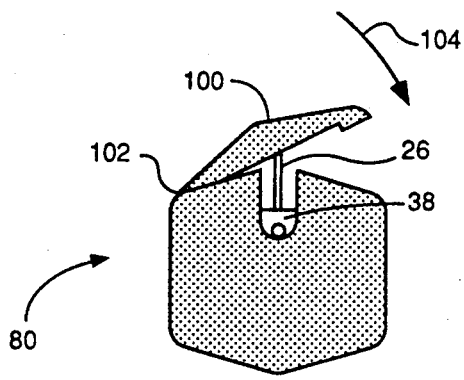
FIG. 8 is an end view of a biopsy needle driving unit with the needle and spacer assembly of FIG. 6 mounted thereto and illustrating how the biopsy needle spacer prevents the cover of the driving unit from being closed.

FIG. 8 is a front view of the driving unit 80 with the biopsy needle assembly 38 and biopsy needle spacer 10 mounted thereto. At the top of the housing 82 is a lid 100 which is hinged on the left side 102 as shown in FIG. 8 so that the lid pivots in the direction indicated by the arrow 104. The lid 100 provides a means for accessing the interior of the driving unit 80 to couple a biopsy needle assembly 38 to the slides 86, 88 mounted therewithin. As can be seen in FIG. 8, when the biopsy needle assembly 38 is coupled to the driving unit 80 with the biopsy needle spacer 10 still mounted thereto, the upwardly projecting fin 26 of the biopsy needle spacer extends above the top of the housing 82 and prevents the lid 100 from being closed. Thus, to close the lid 100, it is necessary first for the biopsy needle spacer 10 to be removed. In this manner, the physician will immediately recognize that the biopsy needle spacer 10 is still installed on the biopsy needle assembly 38 and will not attempt to fire the unit without first removing the spacer.

The operation of the biopsy needle spacer 10 to facilitate the use of a dual stage, spring-propelled, automated tissue sampling instrument in conjunction with CT-scan will now be discussed. The biopsy needle spacer 10 is mounted to the biopsy needle assembly 38, the spacer being received between the cannula needle head 60 and the stylet needle head 70, the stylet shaft 50 rearward of the cannula needle head 60 being received within the slot 30 in the biopsy needle spacer, and the rear transverse flange 66 of the cannula needle head 60 being received within the recess 24 in the face 22 of the flange 20 of the biopsy needle spacer. With the biopsy needle spacer 10 thus installed, the stylet 42 and cannula 40 are held in predetermined relationship wherein the sharpened stylet tip 52 projects from the forward end 46 of the cannula. In this configuration, the predetermined spaced apart relation between the needle heads 60, 70 also corresponds to the spacing between the slides 86, 88 of the driving unit 80. With the biopsy needle spacer 10 mounted to the biopsy needle assembly 38, the physician manually introduces the needle assembly 38 into the body of the patient and guides the forward end of the needle assembly to a point adjacent the target tissue. The patient is then rescanned to verify the location of the tip of the needle assembly 38 with respect to the target tissue. If necessary, the biopsy needle assembly 38 is repositioned, and the patient is rescanned. When the tip of the needle assembly is properly positioned within respect to the target tissue and the needle location has been verified, the cocked driving unit 80 is mounted to the needle assembly 38 with the spacer 10 still attached. Since the biopsy needle spacer 10 maintains the needle heads 60, 70 at a predetermined spaced apart interval corresponding to the distance between the cocked slides 86, 88 of the drive mechanism 80, the needle heads couple easily to the slides of the drive unit. The biopsy needle spacer 10 is then removed, and the instrument is ready for firing. To ensure that the physician does not attempt to fire the instrument without first having removed the biopsy needle spacer 10, the upwardly projecting fin 26 of the spacer will prevent the lid 100 of the housing 82 of the driving unit 80 from being closed until the needle spacer has been removed.

An advantage of forming the needle spacer of a relatively soft and flexible material is that removal of the spacer from the needle assembly is facilitated. As the needle spacer 10 is removed from the biopsy needle assembly 38, if the physician exerts a force at a slight angle to the slot 30 of the needle spacer, a rigid spacer would tend to dislodge the needle assembly from the driving unit 80. By molding the spacer 10 from a soft and flexible material, the spacer will tend to flex and peel away from the needle assembly, rather than dislodging the needle assembly from the driving unit.

Figure 9:
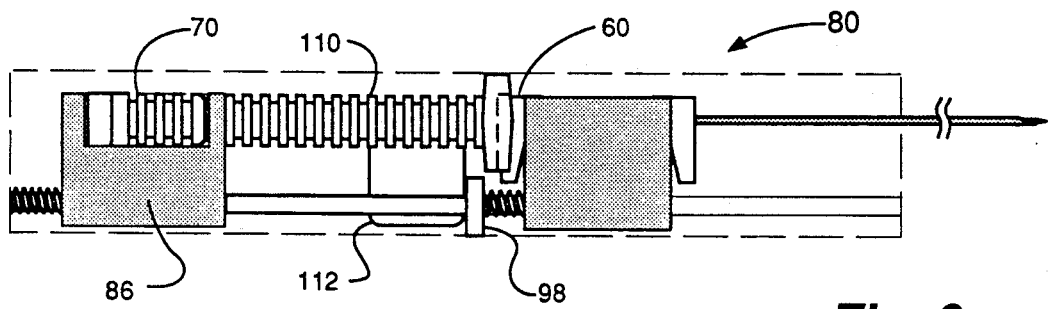
FIG. 9 is a side view of a first alternate embodiment of a needle spacer according to the present invention as mounted to a biopsy needle assembly and with the spacer and needle assembly mounted to a driving unit.

FIG. 9 illustrates a first alternate embodiment of a needle spacer 110 according to the present invention. The first alternate embodiment 110 works on a different principle than the preferred embodiment of the biopsy needle spacer 10 in that, rather than preventing the lid of the housing from being closed while the biopsy needle spacer is still mounted to the needle assembly, the needle spacer 110 instead prevents the instrument from being fired. In place of the upwardly directed fin 26 of the preferred embodiment 10, the first alternate embodiment 110 includes a downwardly directed flange 112 configured to abut the intermediate wall 98 of the driving unit 80. Thus, if the physician attempts to fire the instrument with the needle spacer 110 still mounted to the needle assembly 38, the interference engagement between the downwardly directed flange 112 and the intermediate wall 98 of the driving unit 80 will prevent the slide 86 from advancing. Thus, when the physician presses the trigger to fire the unit, nothing will happen. The physician will then know to open the lid 100 of the housing 82 and remove the biopsy needle spacer 110.

Since the interference engagement between the downwardly directed flange 112 and the intermediate wall 98 of the driving unit must be sufficiently rigid to withstand the force of the rear spring 90 driving the first carriage 86, it is preferable that the biopsy needle spacer 110 of the first alternate embodiment be formed from a more rigid material than the biopsy needle spacer 10 of the preferred embodiment. Thus, the biopsy needle spacer 110 of the first alternate embodiment is comprised of a rigid nylon, such as the material from which the needle heads 60, 70 of the biopsy needle assembly 38 are formed. However, it will again be understood that the particular composition of the biopsy needle spacer 110 is not critical to the invention, and that other suitable materials which permit the spacer 110 to perform its function as described herein may be used instead.

The first alternate embodiment of the biopsy needle spacer 110 is not as advantageous as the preferred embodiment 10 in the sense that it does not prevent the physician from attempting to fire the instrument. Nonetheless, the first alternate embodiment 110 affords advantages over the prior art in that it eliminates the possibility of the instrument being fired with the needle spacer still in place, in which event both needles would advance simultaneously, rather than sequentially, and no tissue specimen would be retrieved. Since the physician will have felt and heard the slides advancing, he may well presume that a satisfactory tissue specimen was retrieved and would not realize that the needle spacer was in place until after the needle had been withdrawn from the patient.

Figure 10:
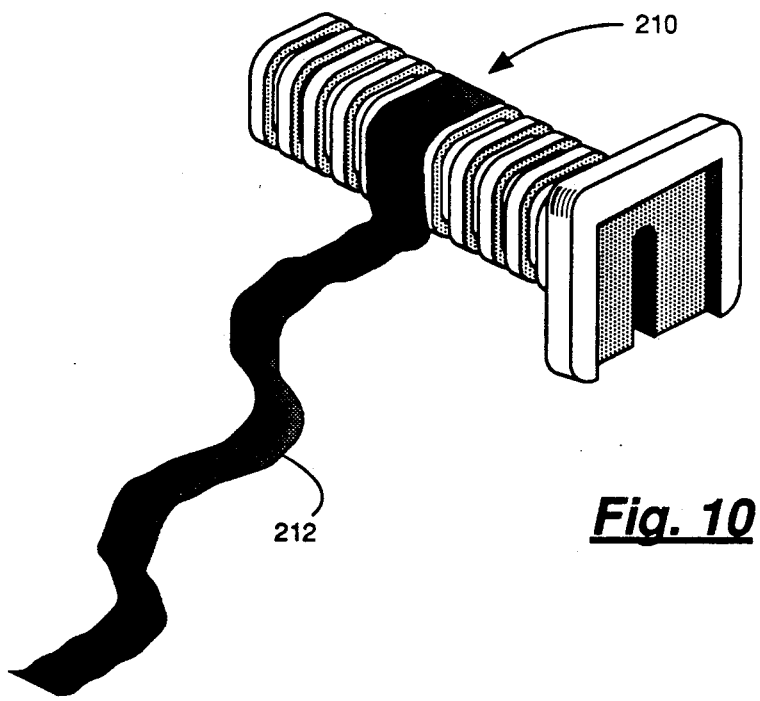
FIG. 10 is a perspective view of a second alternate embodiment of a needle spacer according to the present invention.

FIG. 10 shows a second alternate embodiment of a needle spacer 210 according to the present invention. This embodiment 210 works on a principle different from either the preferred embodiment 10 or the first alternate embodiment 110 in that it neither prevents the lid 100 of the housing 82 from being closed nor prevents the needles 40, 42 from advancing. The second alternate embodiment 210 does not have either an upwardly projecting fin or a downwardly extending flange, but instead includes a length of ribbon 212 attached to the body of the spacer. Preferably, the ribbon 212 is brightly colored, such as red or yellow, to indicate "stop" or "caution." When the biopsy needle assembly 38 is mounted to the driving unit 80 with the needle spacer 210 of the second alternate embodiment mounted thereto, the length of ribbon 212 will hang outside the housing 82. Thus, even if the physician closes the lid 100 of the housing 82, the length of colored ribbon 212 hanging outside the housing will provide a readily visible indicator to the physician that the needle spacer 210 is still mounted. Another advantage of the ribbon 212 is that if the clearance between the spacer 210 and the walls of the housing 82 is especially tight, or if the physician has large fingers, the ribbon can also provide a convenient means which the user can grasp to pull the spacer member 210 off of the needle assembly 38.

The second alternate embodiment 210 suffers disadvantages with respect to the other two embodiments 10, 110 in that it will neither render it impossible for the physician to attempt to fire the instrument nor prevent the needles from advancing if the physician in fact fires the instrument. Nonetheless, the second alternate embodiment 210 provides significant advantages over the prior art in that, with the length of brightly colored ribbon 212 hanging outside the housing 82, it is much less likely that the physician will forget that the needle spacer 210 is still mounted to the needle assembly 38.

Finally, it will be understood that the preferred embodiment has been disclosed by way of example, and that other modifications may occur to those skilled in the art without departing from the scope and spirit of the appended claims.

What is claimed is:

1. A needle spacer apparatus for use with a needle assembly and a driving unit, said needle assembly comprising a hollow first needle having a forward end and having a first needle head at the rearward end thereof, said needle assembly further comprising a second needle telescopically received within said hollow first needle and having a sharpened tip at the forward end thereof and a second needle head at the rearward end thereof, said first and second needle heads being relatively movable to an operational relationship wherein said sharpened tip of said second needle projects slightly beyond said forward end of said hollow first needle, said needle assembly being capable of being selectively coupled to said driving unit for effecting relative movement of said needles, and said driving unit comprising a housing having a lid which can be selectively opened to permit said needle assembly to be coupled to said driving unit, said needle spacer apparatus comprising:

means selectively mountable to said needle assembly for maintaining said needle heads in said operational relationship, said means being configured to permit said needle assembly to be coupled to said driving unit with said means mounted thereto, and said means further being configured to prevent said lid of said housing of said driving unit from being closed while said means is mounted to said needle assembly;

whereby a user will not attempt to actuate said driving unit with said needle spacer apparatus mounted to said needle assembly.

2. The needle spacer apparatus of claim 1, wherein said means for maintaining said needle heads in said operational relationship comprises a body member selectively mountable to said needle assembly between said first and second needle heads.

3. The needle spacer apparatus of claim 2, wherein said body member comprises a longitudinal slot formed therein so as to receive therewithin a portion of said second needle lying between said first and second needle heads when said first and second needle heads are in said operative relationship.

4. The needle spacer apparatus of claim 2, wherein said body member comprises means at the forward end thereof for engaging said first needle head to mechanically couple said body member to said first needle head.

5. The needle spacer apparatus of claim 2, wherein said body member comprises an upwardly projecting fin which, when said needle assembly is coupled to said driving unit, engages said lid of said housing to prevent said lid from being closed while said body member is mounted to said needle assembly.

6. A needle spacer apparatus for use with a needle assembly and a driving unit, said needle assembly comprising a hollow first needle having a forward end and having a first needle head at the rearward end thereof, said needle assembly further comprising a second needle telescopically received within said hollow first needle and having a sharpened tip at the forward end thereof and a second needle head at the rearward end thereof, said first and second needle heads being relatively movable to an operational relationship wherein said sharpened tip of said second needle projects slightly beyond said forward end of said hollow first needle, said needle assembly being capable of being selectively coupled to said driving unit for effecting relative movement of said needles, said needle spacer apparatus comprising:

means selectively mountable to said needle assembly for maintaining said needle heads in said operational relationship, said means being configured to permit said needle assembly to be coupled to said driving unit with said means mounted thereto, and said means further being configured to interferingly engage said driving unit to prevent said driving unit from effecting movement of said needles while said means is mounted to said needle assembly;

whereby if a user attempts to actuate said driving unit with said needle spacer apparatus mounted to said needle assembly, said driving unit will not operate.

7. The needle spacer apparatus of claim 6, wherein said means for maintaining said needle heads in said operational relationship comprises a body member selectively mountable to said needle assembly between said first and second needle heads.

8. The needle spacer apparatus of claim 7, wherein said body member comprises a longitudinal slot formed therein so as to receive therewithin a portion of said second needle lying between said first and second needle heads when said first and second needle heads are in said operative relationship.

9. The needle spacer apparatus of claim 7, wherein said body member comprises means at the forward end thereof for engaging said first needle head to mechanically couple said body member to said first needle head.

10. The needle spacer apparatus of claim 7, wherein said body member comprises a downwardly projecting fin which, when said needle assembly is coupled to said driving unit, engages an intermediate wall of said driving unit to prevent said needles from being advanced while said body member is mounted to said needle assembly.

11. A needle spacer apparatus for use with a needle assembly and a driving unit, said needle assembly comprising a hollow first needle having a forward end and having a first needle head at the rearward end thereof, said needle assembly further comprising a second needle telescopically received within said hollow first needle and having a sharpened tip at the forward end thereof and a second needle head at the rearward end thereof, said first and second needle heads being relatively movable to an operational relationship wherein said sharpened tip of said second needle projects slightly beyond said forward end of said hollow first needle, said needle assembly being capable of being selectively coupled to said driving unit for effecting relative movement of said needles, and said driving unit comprising a housing having a lid which can be selectively opened to permit said needle assembly to be coupled to said driving unit, said needle spacer apparatus comprising:

means selectively mountable to said needle assembly for maintaining said needle heads in said operational relationship, said means being configured to permit said needle assembly to be coupled to said driving unit with said means mounted thereto, and said means further being configured to be visible from outside said housing while said means is mounted to said needle assembly even when said lid of said housing is closed;

whereby said means being visible from outside said housing provides a readily visible indicator to a user even when said lid of said housing is closed that said means is still mounted to said needle assembly.

12. The needle spacer apparatus of claim 11, wherein said means for maintaining said needle heads in said operational relationship comprises a flag attached thereto which will hang outside said housing when said means is mounted to said needle assembly and said lid of said housing is closed.

13. The needle spacer apparatus of claim 12, wherein said flag comprises a length of ribbon.

14. The needle spacer apparatus of claim 13, wherein said flag is brightly colored to enhance its visibility.

15. The needle spacer apparatus of claim 11, wherein said means for maintaining said needle heads in said operational relationship comprises a body member selectively mountable to said needle assembly between said first and second needle heads.

16. The needle spacer apparatus of claim 15, wherein said body member comprises a longitudinal slot formed therein so as to receive therewithin a portion of said second needle lying between said first and second needle heads when said first and second needle heads are in said operative relationship.

17. The needle spacer apparatus of claim 15, wherein said body member comprises means at the forward end thereof for engaging said first needle head to mechanically couple said body member to said first needle head.

* * * * *